United States Patent
Lathuiliere et al.

(10) Patent No.: US 9,950,149 B2
(45) Date of Patent: Apr. 24, 2018

(54) BIOMOLECULAR CELL ENCAPSULATION DEVICE AND METHODS OF IMPLANTATION

(71) Applicants: Nestec S.A., Vevey (CH); Ecole Polytechnique Federale de Lausanne (EPFL), Lausanne (CH)

(72) Inventors: Aurelien Lathuiliere, Geneva (CH); Nicolas Bouche, Les Paccots (CH); Bernard Schneider, Pully (CH)

(73) Assignees: NESTEC S.A. (CH); ECOLE POLYTECHNIQUE FEDERALE DE LAUSANNE (EPFL) (CH)

( * ) Notice: Subject to any disclaimer, the term of this patent is extended or adjusted under 35 U.S.C. 154(b) by 0 days.

(21) Appl. No.: 14/777,839

(22) PCT Filed: Apr. 24, 2013

(86) PCT No.: PCT/EP2013/058448
§ 371 (c)(1),
(2) Date: Sep. 17, 2015

(87) PCT Pub. No.: WO2014/173441
PCT Pub. Date: Oct. 30, 2014

(65) Prior Publication Data
US 2016/0184569 A1    Jun. 30, 2016

(51) Int. Cl.
*A61M 37/00* (2006.01)
*A61F 2/02* (2006.01)

(52) U.S. Cl.
CPC ............. *A61M 37/00* (2013.01); *A61F 2/022* (2013.01); *A61F 2220/0008* (2013.01); *A61M 2202/09* (2013.01); *A61M 2207/00* (2013.01)

(58) Field of Classification Search
CPC .... A61M 37/00; A61M 2202/09; A61F 2/002
USPC ...................... 435/325, 374, 297.1
See application file for complete search history.

(56) References Cited

U.S. PATENT DOCUMENTS

| | | |
|---|---|---|
| 5,344,454 A | 9/1994 | Clarke et al. |
| 5,529,914 A | 6/1996 | Hubbell et al. |
| 6,060,640 A | 5/2000 | Pauley et al. |
| 6,773,458 B1 | 8/2004 | Brauker et al. |
| 6,911,227 B2 | 6/2005 | Hubbell et al. |
| 7,427,415 B2 | 9/2008 | Scharp et al. |
| 7,432,104 B2 | 10/2008 | Mitalipova et al. |
| 7,510,876 B2 | 3/2009 | D'Amour et al. |
| 7,534,608 B2 | 5/2009 | Martinson et al. |
| 7,695,965 B2 | 4/2010 | Martinson et al. |
| 2010/0121446 A1 | 5/2010 | Bruce et al. |

FOREIGN PATENT DOCUMENTS

| | | |
|---|---|---|
| JP | 2012-508584 | 4/2012 |
| WO | 92/07525 A1 | 5/1992 |
| WO | 96/10966 A1 | 4/1996 |
| WO | 96/32076 A1 | 10/1996 |
| WO | 20081103101 A1 | 8/2008 |
| WO | 2008/108412 | 9/2008 |
| WO | 20081112190 A1 | 9/2008 |
| WO | 2010/057039 A2 | 5/2010 |
| WO | 20121041320 A1 | 4/2012 |

OTHER PUBLICATIONS

Belaunzaran et al. Chronic Delivery of Antibody Fragments Using Immunoisolated Cell Implants As a Passive Vaccination Tool; PloS One, vol. 6, No. 4 (2011) pp. 1-11.*
International Search Report for PCT/EP2013/058448 dated Jan. 17, 2014.
Brauker et al., "Neovascularization of immunoisolation membranes: The effect of membrane architecture and encapsulated tissue," Transplantation 1: 163, 1992.
Takahashi et al., "Induction of Pluripotent Stem Cells from Adult Human Fibroblasts by Defined Factors," Cell, 131, 861-872, 2007.
Yu et al., "Induced Pluripotent Stem Cell Lines Derived from Human Somatic Cells," Science, 318, 2007, 1917-1920.
Yu et al., "Human Induced Pluripotent Stem Cells Free of Vector and Transgene Sequences," Science, 324, 2009, 797-801.
Zhou et al., "Generation of Induced Pluripotent Stem Cells Using Recombinant Proteins," Cell Stem Cell, 4, 2009, 381-384.
Takahashi et al., "Induction of Pluripotent Stem Cells from Mouse Embryonic and Adult Fibroblast Cultures by Defined Factors," Cell, 126, 663-676, 2006.
Williams et al., "Membrane structure, the bubble point, and particle retention, a new theory," Pharmaceutical Technology, May 1983.
Brauker et al., "Neovascularization at a membrane-tissue interface is dependent on microarchitecture," World Biomaterials Congress, Apr. 24-28, 1992, 685.
Schulz et al., "A Scalable System for Production of Functional Pancreatic Progenitors from Human Embryonic Stem Cells," PLoS One, 7, 2012, e37004.
Notice of Reasons for Rejection, Japanese Patent Application No. P2016-509303, dated Feb. 21, 2017.

* cited by examiner

*Primary Examiner* — Scott Long
*Assistant Examiner* — Paul C Martin
(74) *Attorney, Agent, or Firm* — Bryan Cave LLP

(57) ABSTRACT

Provided herein is a cell encapsulation device comprising an internal chamber suitable for holding biological agents, wherein the internal chamber is disposed between a first semipermeable layer and a second semi-permeable layer, and the first and second semi-permeable layers are mounted on a supporting frame surrounding a perimeter of the internal chamber; wherein the supporting frame comprises a first frame element and a second frame element, and the first and second frame elements co-operate to position the first and second semipermeable layers at a predetermined separation distance between the layers.

33 Claims, 8 Drawing Sheets

DETAIL G

DETAIL J

BIOMOLECULAR CELL ENCAPSULATION DEVICE AND METHODS OF IMPLANTATION

FIELD OF THE INVENTION

The present invention relates to the field of devices for encapsulation of biological agents. In particular, the biological agents can be cells which are suitable for implantation into living animals such as mammals.

BACKGROUND OF THE INVENTION

There is a need for improved encapsulation devices for implantation in vivo. In particular, there is a need for devices which are simple to manufacture, but which have improved biocompatibility compared to existing devices. Moreover, there is a need for devices which improve the viability, maturation and/or differentiation properties and function of biological agents such as encapsulated cells following implantation.

Various biological agents, including cells, can be encapsulated within an implant device comprising a semi-permeable membrane and implanted in vivo. The semi-permeable membrane typically permits access of nutrients, growth factors and small biological agents to the encapsulated cells, but prevents access of cells of the immune system. The semi-permeable membrane also prevents egress of the cells from the encapsulation device. A further function of the implant may be to promote vascularization around the device, in order to increase survival of the cells. Suitable implant devices for encapsulating cells are disclosed, for example, in U.S. Pat. No. 6,060,640 and U.S. Pat. No. 6,773,458.

SUMMARY OF THE INVENTION

Accordingly, in one aspect the present invention provides a cell encapsulation device comprising an internal chamber suitable for holding living cells, wherein the internal chamber is disposed between a first semi-permeable layer and a second semi-permeable layer, and the first and second semi-permeable layers are mounted on a supporting frame surrounding a perimeter of the internal chamber; wherein the supporting frame comprises a first frame element and a second frame element, and the first and second frame elements co-operate to position the first and second semi-permeable layers at a predetermined separation distance between the layers.

In one embodiment, the first semi-permeable layer is mounted on the first frame element and the second semi-permeable layer is mounted on the second frame element, and the first and second frame elements interconnect to enclose the perimeter of the internal chamber.

Preferably each of the first and second frame elements comprises (a) a mounting region to which the first or second semi-permeable layer is attached and (b) a spacer region, such that when the first and second frame elements interconnect the spacer regions are positioned between the mounting regions and together define the predetermined separation distance between the layers.

In one embodiment, the supporting frame further comprises a loading port, through which substances and/or cell suspension can be introduced into the internal chamber. In another embodiment, the device comprises an adhesive seal between the first and/or second semi-permeable layer and the supporting frame.

Preferably the first and second frame elements are ultrasonically welded together. In another preferred embodiment, the first and/or second semi-permeable layer is ultrasonically welded to the frame.

In one embodiment, the first and second semi-permeable layers each comprise a membrane layer in contact with the internal chamber and a mesh layer overlying the membrane layer to the exterior of the internal chamber. Preferably the membrane layer comprises polypropylene, polycarbonate, polyethyleneterephthalate or polytetrafluoroethylene. Preferably the mesh layer comprises mesh layer comprises nylon, titanium, stainless steel, polyethylene terephthalate, polytetrafluoroethylene or polyester.

In one embodiment, mammalian cells are encapsulated in the internal chamber. Preferably the encapsulated cells are human cells. More preferably the encapsulated cells are derived from induced pluripotent stem cells (iPSCs), e.g. the encapsulated cells are cells which have been at least partially differentiated from iPSCs before encapsulation. Most preferably the encapsulated cells are pancreatic progenitor cells.

In another embodiment, the cells encapsulated in the chamber are capable of producing and/or secreting a therapeutic agent. The therapeutic agent may be, for example, a therapeutic protein, peptide, nucleic acid or other biologically active agent. In particular embodiments, the therapeutic agent may be an antibody or fragment thereof, a DNA molecule or an RNA molecule. The cells may be engineered to produce the therapeutic agent using recombinant DNA techniques, e.g. the cells may be recombinant cells expressing an exogenous polypeptide or other therapeutic agent.

In a further aspect, the present invention provides a method for producing a cell encapsulation device according to any preceding claim, comprising mounting first and second semi-permeable layers on a supporting frame to enclose an internal chamber within the device, wherein the supporting frame comprises a first frame element and a second frame element, and the first and second frame elements position the first and second semi-permeable layers at a predetermined separation distance between the layers.

In one embodiment, the method comprises mounting the first semi-permeable layer on the first frame element, mounting the second semi-permeable layer on the second frame element, and engaging the first and second frame elements to enclose the perimeter of the internal chamber.

In a further aspect, the present invention provides a method for differentiating cells, comprising encapsulating the cells in a device as defined above, and implanting the device into a living mammal.

In one embodiment the mammal is non-human, and the encapsulated cells are human cells. In another embodiment, the mammal is human and the encapsulated cells are human.

In another embodiment, the mammal is non-human, and the encapsulated cells are non human cells.

In a further aspect, the present invention provides a method for preventing or treating diabetes in a subject in need thereof, comprising implanting a device as defined above comprising pancreatic progenitor cells into the subject.

In one embodiment, the pancreatic progenitor cells differentiate into functional glucose-responsive pancreatic islet cells after implantation into the subject.

In some embodiments of the methods defined above, the device is implanted subcutaneously. In alternative embodiments, the device may be implanted at an intrathecal, intracerebral, or intraperitoneal site.

In a further aspect, the present invention provides use of a device as defined above, for differentiating encapsulated cells in a mammal in vivo.

DETAILED DESCRIPTION OF THE INVENTION

Figure 1:
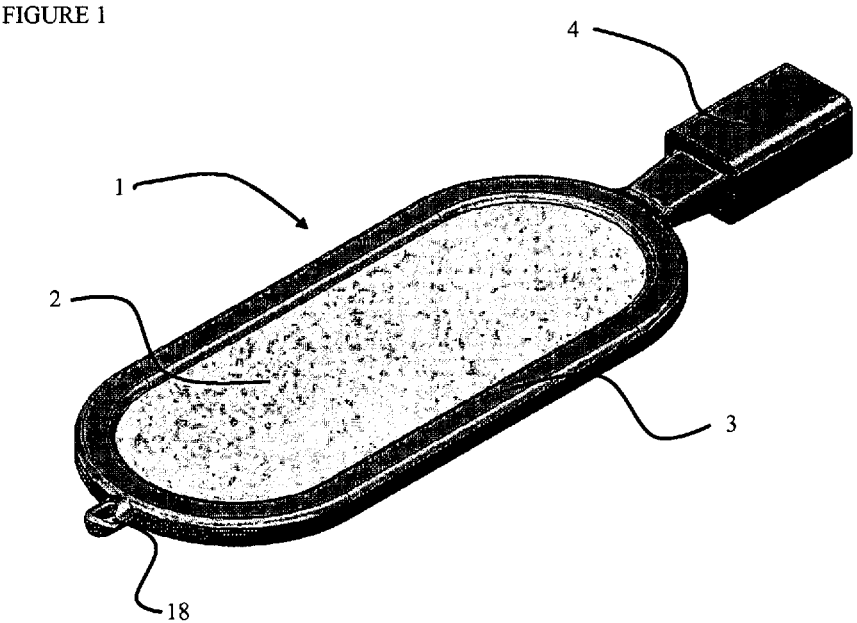
FIG. 1 shows a perspective view of one embodiment of an encapsulation device an encapsulation device as described herein.

In embodiments of the present invention, the semi-permeable layers which contain the cells within the chamber are mounted on a supporting frame structure, which precisely positions the layers at a predetermined separation corresponding to the depth of the internal chamber. The frame typically entirely encloses the edges of the semi-permeable layers at the perimeter of the internal chamber, which avoids the presence of rough edges of the semi-permeable layers on the external surfaces of the device and improves biocompatibility. Advantageously, the supporting frame may be formed from only two elements which interconnect to define the spacing between the layers and to hold them in place. This avoids the need for a separate spacer between the layers, which simplifies the manufacturing method and contributes to the provision of a smooth external surface on the device. The frame may also comprise an integrated loading port, which facilitates the introduction of substances into the internal chamber of the device and may simplify the manufacturing process.

Cell Encapsulation Device

Embodiments of the present invention relate to encapsulation devices for holding living cells. Such devices can typically be implanted into an animal such as a mammal, including a human. In one embodiment, the device comprises a biocompatible, immune-isolating device that is capable of wholly encapsulating cells therein, optionally in combination with one or more biologically active agents.

The cells are held in a chamber within the device. Typically the chamber is fully enclosed, e.g. comprises a continuous wall structure surrounding the cells, such that the cells cannot escape from the chamber.

In some embodiments the cells may be enclosed within or disposed on a biocompatible matrix material within the chamber, such as a hydrogel. Suitable matrix materials include polyvinyl alcohol (PVA), alginate, agarose, gelatin, collagen, polyethylene glycol, fibrin and chitosan. The matrix may be in the form of e.g. a gel, microbeads or a sponge. The matrix may be added to the chamber during manufacture of the device (i.e. before the cells are introduced into the chamber), or alternatively the matrix may be added to the chamber at the same time as loading of the cells. In some embodiments, the cells may first be combined with the matrix (e.g. to porous microbeads), and then the matrix comprising the cells loaded into the chamber.

The embodiments of the encapsulation devices described herein are not intended to be limited to certain device size, shape, design, volume capacity, and/or materials used to make the encapsulation devices, except as otherwise defined herein in the independent claims.

Cells

Cells that may be encapsulated into the devices described herein can include any type of animal cells, preferably mammalian cells, or human cells. Typically the cells may be of therapeutic benefit to a subject upon implantation. Suitable cells include allogeneic and xenogeneic cells, autologous cells or derivatives thereof. For example, it may be desirable to obtain stem cells or somatic cells from a subject and derive a therapeutic cell population from those cells. Such a process typically reduces the risk of an immune response to the implanted cells. Exemplary cell types suitable for use in the encapsulation devices include aggregated or single cell suspensions of pluripotent stem cells or derivatives thereof, preferably induced pluripotent stem (iPS) cells, more preferably human induced pluripotent stem (hiPS) cells. In particular embodiments, the cells may comprise pancreatic progenitor cells, glucose responsive beta cells, insulin producing cells, definitive endoderm cells, islet cells, tumor cells, or any combination thereof.

Induced pluripotent stem (iPS) cells are pluripotent stem cells derived from a non-pluripotent cell. See Zhou et al. (2009), Cell Stem Cell 4:381-384; Yu et al., (2009) Science 324(5928):797-801, Epub Mar. 26, 2009; Yu et al. (2007) Science 318(5858):1917-20, Epub Nov. 20, 2007; Takahashi et al., (2007) Cell, 131:861-72; and Takahashi K. and Yamanaka S. (2006), Cell 126:663-76. The animals from which the non-pluripotent cells are harvested may be vertebrate or invertebrate, mammalian or non-mammalian, human or non-human. Examples of animal sources include, but are not limited to, primates, rodents, canines, felines, equines, bovines and porcines. The pluripotent cells can be passaged using any method known to those of skill in the art, including, manual passaging methods, and bulk passaging methods such as enzymatic or non-enzymatic passaging.

In one embodiment of the invention, the cells are generated by differentiation of human induced pluripotent stem cells into a cell type which can be further differentiated into pancreatic, hepatic and other cells, tissues and organs. For instance, definitive endoderm can be differentiated in vitro into pancreatic progenitors cells that will produce insulin in vivo, for treating insulin-dependent Type 1 and Type 2 diabetics (see e.g. U.S. Pat. No. 7,534,608, U.S. Pat. No.

7,510,876 and U.S. Pat. No. 7,695,965). Further suitable cell types for encapsulation include PDX1-negative foregut endoderm cells, foregut endoderm cells or gut endoderm cells; PDX1-positive, dorsally-biased, foregut endoderm cells, PDX1-positive foregut endoderm cells, or PDX1-positive endoderm; pancreatic progenitors, PDX1-positive pancreatic endoderm cells, PDX1-positive pancreatic progenitors, pancreatic epithelium cells, PDX1-positive pancreatic endoderm tip cells, pancreatic endocrine precursor cells, pancreatic endocrine progenitor cells, pancreatic endocrine cells, pancreatic hormone secreting cells, pancreatic islet hormone-expressing cells, or equivalents thereof.

Such cell types are defined by expression of combinations of particular cell surface or other markers, e.g. as defined in WO 2010/057039. Methods to measure the expression of a molecule are well known to those of ordinary skill in the art, and include without limitation, Northern blotting, RT-PCR, in situ hybridization, Western blotting, and immunostaining. Pancreatic islet hormone-expressing cells can be mature or immature, and can be distinguished based on expression of cellular markers and functional properties. Such cells can be poly-hormonal or singly-hormonal, e.g. expressing one or more pancreatic hormones such as insulin, glucagon, ghrelin, somatostatin and pancreatic polypeptide or combinations thereof.

In some embodiments, the cells which are encapsulated may be pluripotent, multipotent, oligopotent or even unipotent. In certain embodiments, the encapsulated cells are pluripotent differentiable cells. Preferably the cells which are encapsulated in the device are pluripotent or progenitor cells which are capable of further differentiation into at least partially mature cells. As used herein, "partially mature cells" may include cells which are not terminally differentiated. For instance, partially mature cells may exhibit at least one characteristic phenotype, such as morphology or protein expression, of a mature cell from the same organ or tissue but can further differentiate into at least one other cell type. For example, a normal, mature hepatocyte typically expresses such proteins as albumin, fibrinogen, alpha-1-antitrypsin, prothrombin clotting factors, transferrin, and detoxification enzymes such as the cytochrome P-450s, among others. Thus, as used herein, a "partially mature hepatocyte" may express albumin or another one or more proteins, or begin to take the appearance or function of a normal, mature hepatocyte.

In further embodiments, the encapsulated cells may be obtained from placental or chorion tissue, or from more mature tissue including, but not limited to adipose, bone marrow, nervous tissue, mammary tissue, liver tissue, pancreas, epithelial, respiratory, gonadal and muscle tissue. In specific embodiments, the encapsulated cells are adult stem cells. In other embodiment the encapsulated cells are placental- or chorionic-derived stem cells.

The cells may be harvested from any type of animal, e.g. vertebrate or invertebrate, mammalian or non-mammalian, human or non-human. Examples of animal sources include, but are not limited to, primates, rodents, canines, felines, equines, bovines and porcines.

In some embodiments, pluripotent cells may first be at least partially differentiated in vitro before encapsulation in the device. Typically, cells can be differentiated in vitro through contact with a cell differentiation environment. A cell differentiating medium or environment may be utilized to partially, terminally, or reversibly differentiate the pluripotent cells described herein. For instance, the medium of the cell differentiation environment may contain a variety of components including, for example, KODMEM medium (Knockout Dulbecco's Modified Eagle's Medium), DMEM, Ham's F12 medium, FBS (fetal bovine serum), FGF2 (fibroblast growth factor 2), KSR or hLIF (human leukemia inhibitory factor). The cell differentiation environment can also contain supplements such as L-Glutamine, NEAA (non-essential amino acids), P/S (penicillin/streptomycin), N2, B27 and beta-mercaptoethanol (beta-ME). It is contemplated that additional factors may be added to the cell differentiation environment, including, but not limited to, fibronectin, laminin, heparin, heparin sulfate, retinoic acid, members of the epidermal growth factor family (EGFs), members of the fibroblast growth factor family (FGFs) including FGF2, FGF7, FGF8, and/or FGF10, members of the platelet derived growth factor family (PDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, high dose activin, and amnionless or variants or functional fragments thereof. TGF/BMP/GDF antagonists could also be added in the form of TGF/BMP/GDF receptor-Fc chimeras. Other factors that may be added include molecules that can activate or inactivate signaling through Notch receptor family, including but not limited to proteins of the Delta-like and Jagged families as well as inhibitors of Notch processing or cleavage, or variants or functional fragments thereof. Other growth factors may include members of the insulin like growth factor family (IGF), insulin, the wingless related (WNT) factor family, and the hedgehog factor family or variants or functional fragments thereof. Additional factors may be added to promote mesendoderm stem/progenitor, endoderm stem/progenitor, mesoderm stem/progenitor, or definitive endoderm stem/progenitor proliferation and survival as well as survival and differentiation of derivatives of these progenitors.

In a preferred embodiment, the encapsulated cells are pancreatic progenitor cells. Such cells may suitably be produced by in vitro differentiation from induced pluripotent stem cells, e.g. using methods as described in Schulz et al. (May 2012) PLoS ONE 7(5): e37004, and yielding encapsulated functional beta cells in vivo.

Induced pluripotent stem (iPS) cells derived from adult differentiated cells are uniquely suited for cell therapy applications because they are pluripotent and self-renewable. Owing to the large variety of cell types that can arise in differentiating pluripotent stem cell cultures, success in achieving efficient, directed differentiation is critical for therapeutic applications of human pluripotent stem cells. Various growth factors, signaling factors and small molecules may be used to attempt to direct in vitro differentiation of pluripotent stem cells towards intermediate cell types, such as pancreatic lineage cells.

The progression of the differentiable cells to the desired cell lineage, or its maintenance in an undifferentiated state can be monitored by quantitating expression of marker genes characteristic of the desired cell lineage as well as the lack of expression of marker genes characteristic of differentiable cell types. One method of quantitating gene expression of such marker genes is through the use of quantitative PCR (Q-PCR). Methods of performing Q-PCR are well known in the art. Other methods that are known in the art can also be used to quantitate marker gene expression. Marker gene expression can be detected by using antibodies specific for the marker gene of interest.

The cells to be encapsulated in the chamber do not necessarily require further differentiation in vivo following implantation. For example, in further embodiments the cells may already be fully differentiated at the time of encapsulation. The cells may be derived from any source, including cell lines or cell types which are not pluripotent. For instance, in some embodiments, the encapsulated cells may be engineered to produce and/or secrete a therapeutic agent such as a polypeptide (e.g. an antibody, growth factor or peptide hormone) or a polynucleotide (e.g. a DNA or RNA molecule). Thus the encapsulated cells may be derived from recombinant cell lines which express an exogenous polypeptide or other therapeutic agent.

Semi-Permeable Layers

The internal chamber is disposed between first and second semi-permeable layers. Each semi-permeable layer may be comprised of one or more sub-layers, e.g. each semi-permeable layer may comprise a laminar structure. In some embodiments, only one of the sub-layers is semi-permeable.

In one embodiment, the semi-permeable layers have a pore size such that oxygen and other molecules important to cell survival and function can move through the semi-permeable layers, but the cells (e.g. the encapsulated cells and/or cells of the host immune system) cannot permeate or traverse through the pores.

In embodiments where the device further encapsulates one or more biologically active agents, e.g., an angiogenic factor, a growth factor or a hormone, the semi-permeable layer preferably additionally allows the encapsulated biologically active substance of interest to pass through the layer, in order to provide access to the target cells outside the device in the host tissue or organism.

In a preferred embodiment, the semi-permeable layer allows one or more nutrients present in the subject to pass through the layer to provide essential nutrients to the encapsulated cells. For example, in one embodiment where the encapsulated cells are insulin-producing pancreatic beta cells or their precursors, the semi-permeable layer allows glucose and oxygen to stimulate the insulin-producing cells to release insulin, while preventing immune system cells from recognizing and destroying the implanted cells. In a preferred embodiment, the semi-permeable membrane prohibits the implanted cells from escaping encapsulation.

Preferably the semi-permeable layer (or one or more sub-layers thereof) is comprised of a biocompatible material that functions under physiologic conditions, particularly physiological pH and temperature. Examples of suitable materials that may be used in the semi-permeable layer include, but are not limited to, polyester, polypropylene, polycarbonate, polyethylene terephthalate (PET), anisotropic materials, polysulfone (PSF), nano-fiber mats, polyimide, tetrafluoroethylene/polytetrafluoroethylene (PTFE; also known as Teflon®), ePTFE (expanded polytetrafluoroethylene), polyacrylonitrile, polyethersulfone, acrylic resin, cellulose acetate, cellulose nitrate, polyamide, as well as hydroxylpropyl methyl cellulose (HPMC) membranes. Suitable materials are manufactured by, for example, Gore®, Phillips Scientific®, Zeus®, Pall® and Dewal®.

Preferably the semi-permeable layer is chemically inert or non-toxic with respect to the cells encapsulated inside the device and/or the host tissue or organism. The semi-permeable layer preferably permits secretion or release of a biologically active agent (which is produced by the encapsulated cells or encapsulated with the cells) across the device, and preferably promotes rapid kinetics of macromolecule diffusion. In further embodiments, the semi-permeable layer may promote long-term stability of the encapsulated cells. For instance, the semi-permeable layer may promote vascularization of the device and thus enhance access of nutrients and oxygen to the encapsulated cells.

In some embodiments, the semi-permeable layer comprises two or more sub-layers, e.g. is a laminar structure. For instance, the semi-permeable layer may be a laminated structure comprising 2, 3 or 4 sub-layers. In a particularly preferred embodiment, the semi-permeable layer comprises a first sub-layer which is in contact with the internal chamber and a second sub-layer which overlies the first sub-layer to the exterior of internal chamber, i.e. the first sub-layer lies on the inside and the second sub-layer lies on the outside of the device.

Preferably the first sub-layer comprises a membrane which is compatible with the cells inside the chamber, and which has a pore size which permits solute transport but prevents entry or egress of cells. Suitably the pore size of the membrane should be less than about 2 μm (i.e. 2 microns), in order to prevent the ingress of vascular structures. More preferably, pore sizes less than about 0.6 μm (i.e. 0.6 microns) are preferred, in order to prevent the access of cells (including macrophages, foreign body giant cells, and fibroblasts) to the internal chamber of the device. Smaller pore sizes should be used where the device encapsulated cells which may be particularly vulnerable to immune attack, e.g. in the case of xenografts or allografts. In the case of isografts (autologous implants), the pore size should be sufficient to prevent the encapsulated cells from exiting the chamber. By "pore size" it is meant the maximum pore size of the material. Pore size may be determined using conventional bubble point methodology, as described in e.g. Pharmaceutical Technology, May 1983, pages 36 to 42.

Preferably the membrane layer comprises polypropylene, polycarbonate, PET or PTFE. For instance, in one embodiment, a semi-permeable PTFE membrane material having a thickness of about 25 microns and a maximum pore size of about 0.4 microns is used. Alternative materials for the membrane layer include polyethylene, cellulose acetate, cellulose nitrate, polyester, nylon, polysulfone materials, cellulose, polyvinylidene difluoride, acrylic, silicone, and polyacrylonitrile.

Preferably the second sub-layer comprises a mesh layer, which typically serves as a vascularization membrane. By "vascularization membrane" it is meant that this sub-layer promotes the growth of vascular structures in host tissue around the device. The second sub-layer may also provide mechanical support or mechanical protection to the first sub-layer.

Vascularization near the host tissue-device interface can be dependent on the nature of the membrane material present in the device. See e.g. Brauker et al., Neovascularization at a membrane-tissue interface is dependent on microarchitecture, Transactions of the Fourth World Biomaterials Congress Apr. 24-28, 1992 p. 685; Brauker, et al., Neovascularization of immunoisolation membranes: The effect of membrane architecture and encapsulated tissue, Transplantation 1:163, 1992.

Accordingly, the second sub-layer preferably comprises a mesh having an average nominal pore size of approximately 0.01 to about 1 mm (i.e. 0.01 to 1 millimeters). Preferably, at least approximately 50% of the pores of the membrane have an average size of approximately 0.01 to about 1 mm.

The mesh layer is typically formed from fibers or strands or a polymer material. These strands are typically elongated structures having one dimension much larger than the other two.

Suitable materials for the mesh layer or vascularization membrane include nylon, polyester and PTFE. In one embodiment the mesh layer is made from nylon and has a pore size of approximately 0.12 mm. Further suitable materials are disclosed, for example, in WO92/07525 and WO96/10966.

Laminated semi-permeable structures for use in cell encapsulation and implantation are disclosed e.g. in U.S. Pat. No. 6,060,640 and U.S. Pat. No. 5,344,454. For instance, a GORE-TEX™ membrane material (which serves as a vascularization-promoting membrane) may be laminated with a BIOPORE™ membrane material (which serves as an immune-isolation membrane for allografts) using a criss-crossing pattern of non-permeable polymeric adhesive.

Support Frame

The device further comprises a supporting frame on which the first and second semi-permeable layers are mounted. The frame provides support to the semi-permeable layers and positions them so as to define the dimensions of the internal chamber. The support frame surrounds a perimeter of the semi-permeable layers, e.g. such that it closes off the space between the layers at the periphery of the internal chamber.

The support frame is typically chemically inert and may function to provide stable mechanical properties to the device. The support frame may also function to maintain the integrity of the device, e.g. by preventing leakage of cells into or out of the device at the perimeter of the semi-permeable layers. The support frame may comprise one or more loading ports to facilitate addition and/or removal of substances to/from the internal chamber. Typically the support frame (and/or semi-permeable layers) can be sterilized.

The support frame may be made from any suitable biocompatible material, preferably durable material which is capable of providing mechanical support to the semi-permeable layers and maintaining the integrity of the device as a whole. The support frame may, for example, be formed from suitable polymer materials such as polypropylene or polyetheretherketone (PEEK), or from a ceramic or metallic material such as titanium, titanium alloy or stainless steel.

In embodiments of the present invention, the support frame is comprised of a first frame element and a second frame element. The first and second frame elements may, for example, engage or interlock mechanically and/or may be welded together to form the overall structure of the support frame. Ultrasonic welding is preferably used to join and/or seal the first and second frame elements. Preferably the first and second frame elements are welded together substantially around the entire perimeter of the support frame.

The first and second frame elements function together to position the first and second semi-permeable layers at a predetermined separation distance between the layers, thereby defining the depth of the internal chamber. For instance, the first semi-permeable layer may be mounted on the first frame element and the second semi-permeable layer on the second frame element. When the first and second frame elements interconnect, they may enclose the perimeter of the internal chamber. This type of arrangement avoids the need for a separate spacer element, simplifies the manufacture of the device and prevents the exposure of rough edges of the semi-permeable membranes to the exterior of the device. Thus in embodiments of the present invention, the external profile of the support frame and the encapsulation device as a whole is as smooth as possible. This improves biocompatibility and thereby the viability of encapsulated cells following implantation in vivo.

In some embodiments, the first and/or second semi-permeable layers may be mounted on the support frame by ultrasonic welding. In further embodiments, an adhesive may be used at the region where the semi-permeable layers abut the support frame. The adhesive may be used to seal the junction between the semi-permeable layers and the frame, for instance to prevent leakage of fluids into or out of the internal chamber. The adhesive may also assist fixation of the semi-permeable layers to the frame, whether or not the semi-permeable layers are also welded ultrasonically to the frame. An adhesive may be used around part or the whole of the periphery of the internal chamber, e.g. along a part or a whole of a perimeter of the first and/or second semi-permeable layers, and/or along a part or a whole of an internal surface of the first and/or second frame elements. Any suitable biocompatible adhesive may be used. In one embodiment, a photo-polymerisable adhesive is used.

The supporting frame may be of any suitable geometry or size, taking into account the considerations set out above. In particular embodiments the support frame may be substantially circular, elliptical or substantially rectangular in shape. Preferably the support frame is a substantially elliptical to rectangular shape. The support frame may vary considerably in size depending on the specific application, but may be, for example, approximately 5 to 100 mm, 10 to 50 mm, 20 to 30 mm or about 25 mm in length.

The support frame, together with the first and second semi-permeable layers which are mounted thereon, may define the geometry of the internal chamber of the device. The internal chamber may form various shapes or conformations, but is typically substantially elliptical to rectangular in shape along a longitudinal axis defined by a long dimension of the support frame, and may be e.g. substantially rectangular in cross-section (i.e. in a transverse axis perpendicular to the longitudinal axis).

The first and second semi-permeable layers typically lie in substantially parallel planes with a relatively narrow separation between the layers. This separation defines a depth of the internal chamber and may be determined by the relative spacing of the mounting positions of the first and second semi-permeable layers on the support frame. In particular embodiments, the separation distance between the first and second semi-permeable layers (i.e. the depth of the internal chamber) may be, for example, 0.05 to 10 mm, 0.2 to 5 mm, 0.3 to 1 mm or 0.4 to 0.8 mm.

Advantageously, embodiments of the present invention allow the first and second semi-permeable layers to be positioned at a precise separation distance. By controlling the depth of the internal chamber in this manner, optimal conditions for differentiation, growth and maintenance of the encapsulated cells can be achieved, according to the precise nature of the cells within the chamber. For instance, the separation distance of the semi-permeable layers can affect the availability of oxygen and other nutrients to cells encapsulated within the internal chamber, since these materials need to diffuse across the semi-permeable layers. Thus cell types which are growing and/or metabolizing at a higher rate (e.g. which have higher oxygen requirements) may need to be encapsulated in a device with a smaller separation distance between the semi-permeable layers, compared to cell types having lower metabolic requirements. Embodiments of the present invention allow the separation distance to be varied and tested for different cell types, and a suitable depth of the chamber selected for optimal viability of the encapsulated cells.

In some embodiments, the support frame may further comprise an anchoring means for holding the encapsulation device in position following implantation in vivo. The anchoring means may comprise, for example, one or more hooks, clamps or other fixing elements suitable for positioning the device in a soft tissue. Alternatively, the anchoring means may comprise one or more holes or cavities in the support frame, through which a suture may be passed to secure the device in vivo.

Encapsulation of Cells in the Device

Once the desired cells have been obtained (e.g. pluripotent or partially differentiated cells, cells which are engineered to express a recombinant product and/or cells which express a therapeutic agent as discussed above), the cells may be introduced into the internal chamber of the device for implantation in vivo. Implantation typically induces (further) differentiation of the cells towards a particular lineage.

For encapsulation into the device, the cells may be prepared in various types of suspension or other fluid formulation. In one embodiment, the cells may be suspended in a suitable fluid medium, such as a growth or differentiation medium. The fluid medium may comprise a physiologically acceptable aqueous solution for the growth or maintenance of the living cells. For example, the fluid medium may comprise glucose, salts, minerals, buffers, amino acids, hormones and growth factors that the cells need and use in vitro and/or in vivo. Suitable fluid media are described, for example, in U.S. Pat. No. 7,432,104.

In one embodiment, the cells are encapsulated using a biocompatible polyethylene glycol (PEG). PEG-based encapsulation is described in more detail in e.g. U.S. Pat. No. 7,427,415, U.S. Pat. No. 6,911,227 and U.S. Pat. No. 5,529,914. The cells may also be encapsulated using any suitable biocompatible matrix or hydrogel, such as polyvinyl alcohol (PVA), alginate, agarose, gelatin, collagen and chitosan.

The cells may be encapsulated in the device at various cell densities. For instance, the encapsulation device may comprise a cell density between about $1\times10^5$ or $1\times10^6$ cells/ml to about $1\times10^{10}$ cells/ml or more. Cells, together with further substances, may be introduced into the device for example via a loading port, which may be integrated into the device and which may provide access to the internal chamber. In some embodiments, the loading port may be sealed (e.g. by means of a plug, adhesive or weld) after introduction of cells into the encapsulation device.

In some cases, it may be desirable to assay the viability and/or functionality of the cells prior to encapsulation to confirm their suitability for use, e.g., in transplantation. This can be accomplished using a variety of methods known in the art. For example, the cells can be stained using vital stains, such as, e.g., trypan blue or ethidium bromide or acridine orange. In preferred embodiments, a population of cells suitable for transplantation is at least about 50%, at least about 75%, at least about 95%, or at least about 99%, viable. In other embodiments, the morphometric characteristics of the cells can be determined as a measure of the suitability of cells for use in implantation.

Alternatively, cells can be assayed for the presence of certain cell surface markers (e.g. pancreatic progenitor or hormone secreting cell markers) or functionality (e.g. production of insulin or other pancreatic hormones) to determine if they are suitable for use in transplantation (see e.g. U.S. Pat. No. 7,534,608).

Implantation of the Device In Vivo

Once the cells have been encapsulated in the device, the device can be implanted into a living animal, e.g. a mammal (such as a human or non-human mammal). The devices may be implanted in various sites, including under the skin (e.g. subcutaneously). Alternatively, the device may be implanted at an intrathecal, intracerebral, intraosseous, or intraperitoneal site.

Typically the device is immobilized at an implantation site to maintain the encapsulated cells at the implantation site and permit diffusion of, for example, an expressed and secreted therapeutic agent from the implantation site. In one embodiment, the implantation site is at, or in close proximity to, a tissue or organ which is focus of the treatment. In other aspects, where delivery of the secreted agent from the device is not location dependent (e.g. where the therapeutic agent may be effectively secreted into the systemic circulation), the device can be implanted in a remote location. For example, in preferred embodiments, the encapsulation device is implanted subcutaneously under the skin on e.g. the forearm, flank, or back, or leg, where it remains until it is surgically removed.

Following implantation, the encapsulated cells typically differentiate towards a particular cell type which provides a useful effect. The differentiated cells found within the device have applications in various fields of research and development including but not limited to drug discovery, drug development and testing, toxicology, production of cells for therapeutic purposes as well as basic science research. Such cell types may express molecules that are of interest in a wide range of research fields, such as cytokines, growth factors, cytokine receptors, extracellular matrix, transcription factors, secreted polypeptides and other molecules, and growth factor receptors.

Thus in one embodiment, non-human mammals implanted with an encapsulation device as described herein may be used as animal models to study disease and/or treatment of disease. Alternatively, the differentiated cells may be extracted from the device (e.g. after removal of the implanted device from the animal) and used for further in vitro applications, e.g. in in vitro studies of disease. In either case, in some embodiments the encapsulated cells may be derived from a different species to the host animal. For example, the encapsulated cells may be human and the host animal may be non-human, e.g. a rodent such as a mouse or rat, or another species of experimental mammal.

In further embodiments, the implanted devices may be used directly in the treatment or prevention of a disease in the host animal. Alternatively, differentiated cells extracted from a first host animal implanted with the device may be used in the treatment of a disease in a second subject animal, e.g. following introduction of the extracted differentiated cells into the second animal. The animal to be treated may be a mammal such as a human.

In particular embodiments, the encapsulated cells may be used in the treatment of a metabolic disorder. For example, diabetes, or one or more symptoms thereof, can be ameliorated or reduced for a period of time following implantation of the device comprising suitable encapsulated cells into a subject suffering from diabetes. In such embodiments, the encapsulated cell is typically a pancreatic progenitor cell or population, a PDX1-positive pancreatic progenitor cell or population, an endocrine precursor cell or population, a poly or singly-hormonal endocrine cell, an insulin-producing pancreatic beta islet cell or any other precursor thereof.

In some embodiments, the cells survive in vivo in the encapsulation device after implantation for at least one hour, one day, one week, one month, three months, six months, or a year or more with a functionality that represents at least 50%, 75%, 95%, or 99% or more of the function expressed at the time of implantation or at the time the cells are fully matured or reach a maximal level of function, e.g. in the case of implantation of progenitor cells which need to further develop or mature to functional cells in vivo. Functionality may be measured typically based on the production or activity of a biological agent of interest, e.g. in the case of pancreatic beta islet cells or their precursors, the production of insulin or an effect on glucose clearance.

The invention will now be further described by way of example only with reference to the following specific embodiments.

Example 1

FIG. 1 shows one embodiment of an encapsulation device 1 according to the present invention. The device 1 comprises first and second semi-permeable layers surrounded by a supporting frame 3. In FIG. 1 only the first (uppermost) semi-permeable layer 2 is visible. The encapsulation device has an overall elliptical to rectangular shape, and further comprises a loading port 4 through which substances (including cells) can be introduced and an anchoring means 18 for positioning the device within a tissue in vivo.

Figure 2:
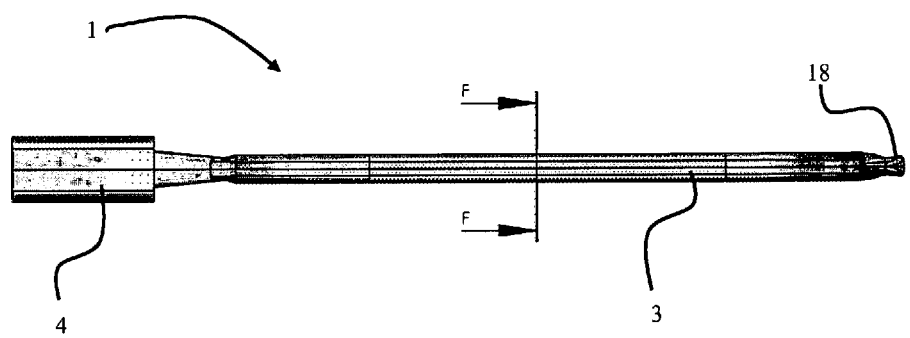
FIG. 2 shows a side view of an encapsulation device as described herein.

FIG. 2 shows a side view of the same encapsulation device 1. The loading port 4 and the anchoring means 18 are integrated into the supporting frame 3. The perimeters of the first and second semi-permeable layers are fully enclosed by the support frame 3, and not visible in FIG. 2.

Figure 3:
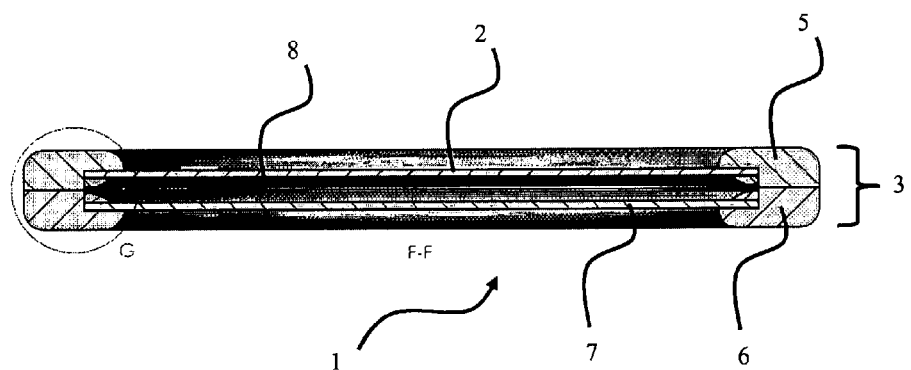
FIG. 3 shows a cross-section view of the encapsulation device at position F shown in FIG. 2.

FIG. 3 shows a cross-section view through the encapsulation device 1 at a position F shown in FIG. 2. The device 1 comprises first and second frame elements 5 and 6 which interconnect to form the supporting frame 3. The first and second semi-permeable layers 2 and 7 are mounted on the support frame 3. The first and second semi-permeable layers 2 and 7 and support frame 3 together enclose an internal chamber 8 within the device.

Figure 4:
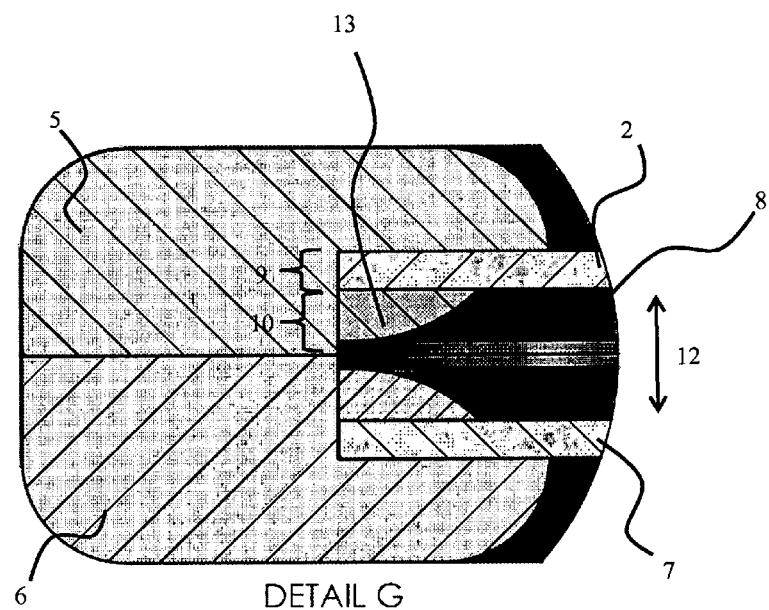
FIG. 4 shows an expanded view of region G of the cross-section view shown in FIG. 3.

FIG. 4 is an expanded view of region G of the cross-section view shown in FIG. 3. The first and second frame elements 5 and 6 engage to form the support frame. The first and second semi-permeable layers are attached to the first and second frame elements 5 and 6 at mounting regions 9 (only the mounting region 9 on the first frame element 5 is labelled). Spacer regions 10 of the first and second frame elements 5 and 6 (only the spacer region 10 on the first frame element 5 is labelled) lie between the mounting regions 9 and together determine a separation distance 12 between the first and second semi-permeable layers 2 and 7. The separation distance 12 defines a depth of the internal chamber 8. An adhesive 13 seals the junction between each of the first and second semi-permeable layers 2 and 7 and the first and second frame elements 5 and 6, particularly at the spacer region 10 (only the adhesive bound to the first frame element 5 and the first semi-permeable layer 2 is labelled).

Figure 5:
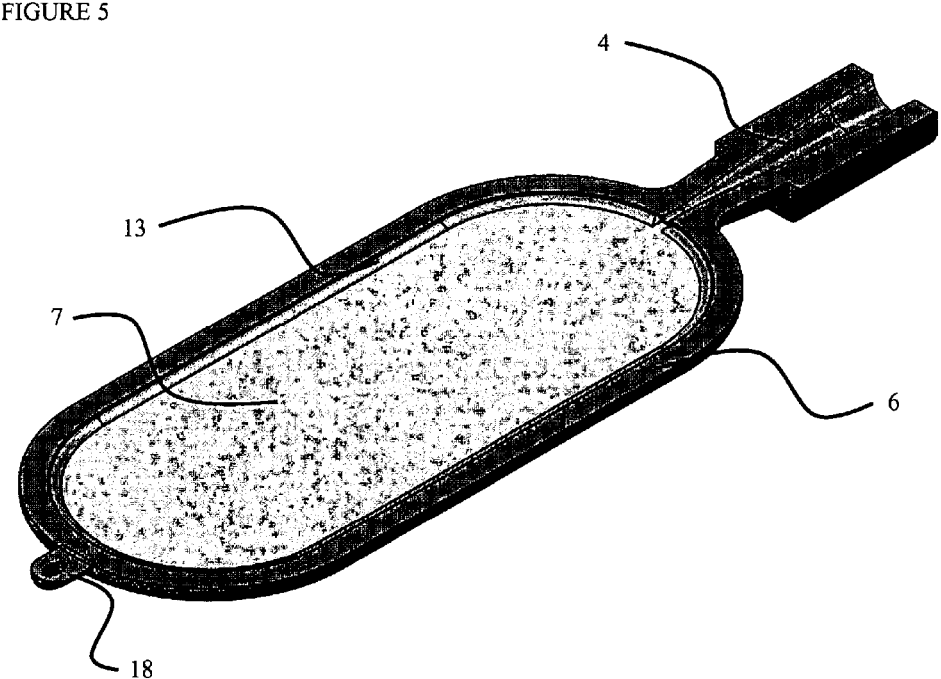
FIG. 5 shows a perspective view of a lower part of an encapsulation device as described herein.

FIG. 5 shows a perspective view of a lower part of the encapsulation device 1, comprising the second frame element 6, second semi-permeable layer 7 mounted thereon and sealed with adhesive 13.

Figure 6:
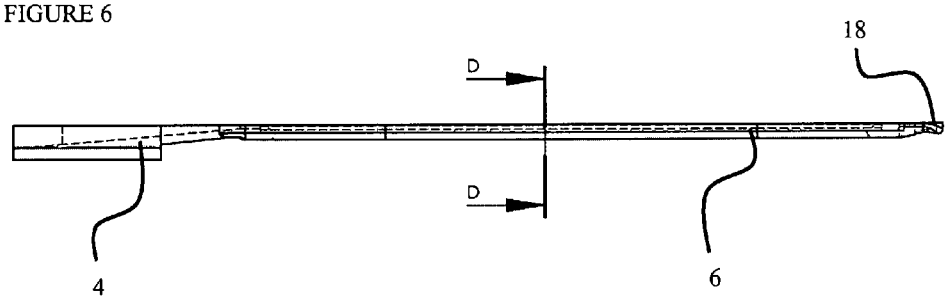
FIG. 6 shows a side view of a lower part of an encapsulation device as described herein.

FIG. 6 shows a side view of the same part of the device.

Figure 7:
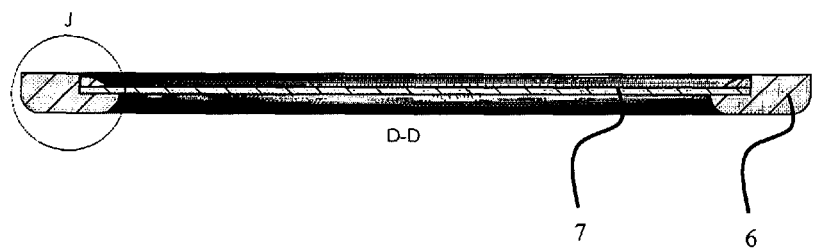
FIG. 7 shows a cross-section view through the lower part of the encapsulation device at a position D shown in FIG. 6.

FIG. 7 shows a cross-section view through the lower part of encapsulation device 1 at a position D shown in FIG. 6.

Figure 8:
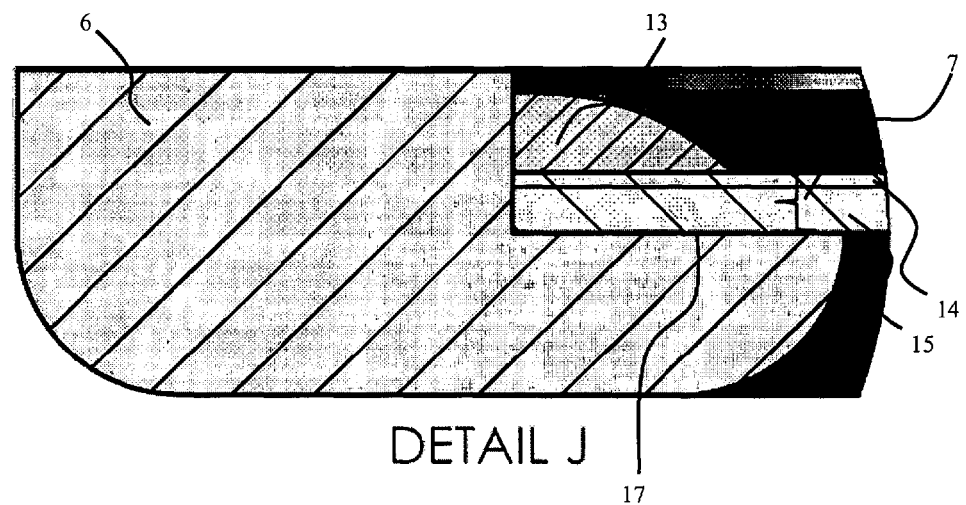
FIG. 8 shows an expanded view of region E of the cross-section view shown in FIG. 7.

FIG. 8 shows an expanded view of region E of the cross-section view shown in FIG. 7. FIG. 8 also illustrates that the second semi-permeable layer 7 is comprised of a membrane layer 14 which bounds the internal chamber 8, and mesh layer 15 which overlies the membrane layer 14 on the external side of the device. The second semi-permeable layer 7 (and specifically the mesh layer 15 thereof) rests on a ledge 17 provided by the second frame element 6. The ledge 17 supports the second semi-permeable layer 7 and together with a corresponding arrangement of the first frame element 5 and first semi-permeable layer 2, defines the separation distance between the layers and the depth of the internal chamber.

Figure 9:
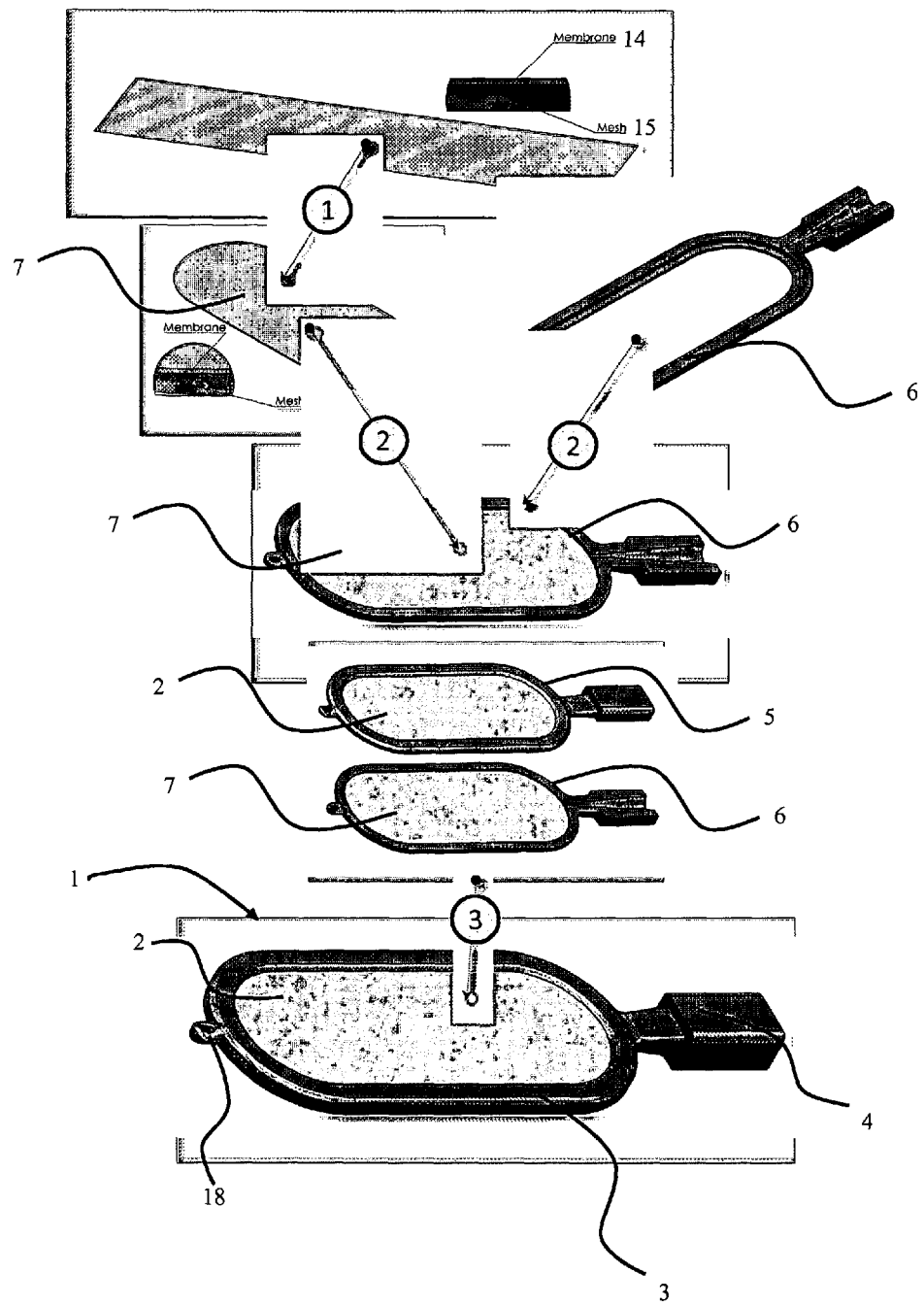
FIG. 9 shows a schematic view of the assembly of an encapsulation device as described herein.

FIG. 9 shows a schematic view of the assembly of encapsulation device 1. At Step 1, a laminated sheet composed of membrane material 14 (e.g. PTFE) and mesh material 15 (e.g. polyester) is cut into the shape of second semi-permeable layer 7. At Step 2, the second semi-permeable layer 7 is welded ultrasonically onto second frame element 6 (made from e.g. polypropylene). In a similar manner, first semi-permeable layer 2 is welded ultrasonically onto first frame element 5 (made from e.g. polypropylene). At Step 3, the first and second frame elements 5 and 6 are then welded together ultrasonically to form the encapsulation device 1, shown with the frame 3 comprising integral loading port 4, integral anchoring means 18 and first semi-permeable layer 2.

Various tools and techniques may be used to cut the membrane 14 and mesh 15 material to a suitable shape, to weld the semi-permeable layers 2 and 7 to the first and second frame elements 5 and 6 and to weld the first and second frame elements 5 and 6 together. For instance, a sonotrode/nest arrangement may be used for ultrasonic welding, wherein the material to be welded is positioned between the sonotrode and nest. In some embodiments, the sonotrode and/or nest may be specifically adapted to precisely position the respective components for welding.

Figure 10:
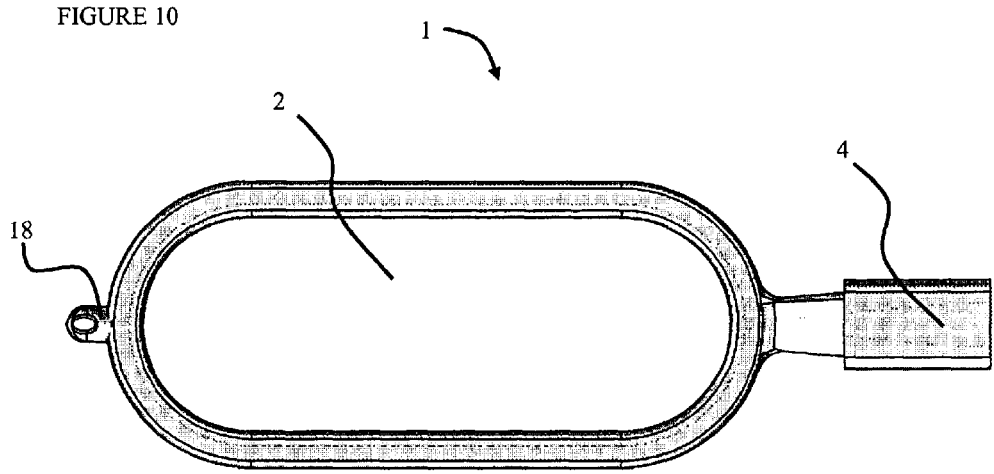
FIG. 10 shows a plan view of an encapsulation device according to the present invention.

FIG. 10 is a plan view of a similar device, showing that the loading port provides access for introducing cells into the internal chamber. In some embodiments, the loading port may be cut and then sealed (e.g. by means of a plug, adhesive or weld) after introduction of cells into the encapsulation device.

Example 2

A renewable source of human beta cells would greatly benefit both fundamental research and cell therapy. Pancreatic progenitors can be differentiated from human pluripotent stem cells in vitro; the subsequent transplantation of pancreatic progenitors cells in vivo results in functional beta cell production. Schulz et al. (May 2012) PLoS ONE 7(5): e37004 discloses a protocol for the differentiation of pancreatic progenitors from a panel of pluripotent stem cell lines, yielding encapsulated functional beta cells in vivo. Using these newly established methods, the partially differentiated cells were encapsulated in a device as described in Example 1 to complete the differentiation of the iPSC-derived pancreatic progenitors in vivo (undifferentiated iPSC lines provided by Cellular Dynamics Inc.).

Figure 11:
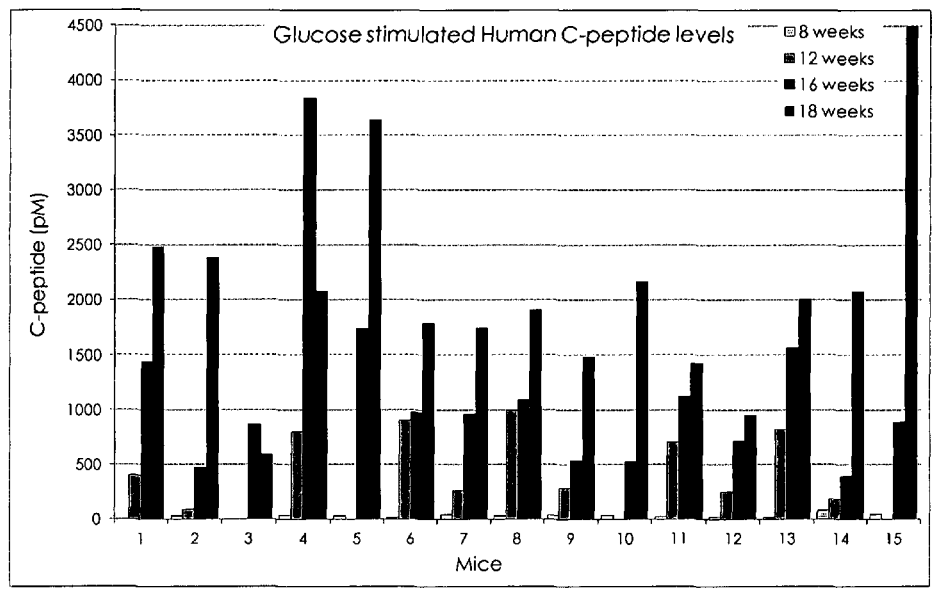
FIG. 11 shows glucose-stimulated human C-peptide levels in mice at various times after implantation with a device as described herein comprising human pancreatic progenitor cells which had been pre-differentiated from human iPSCs.
Figure 12:
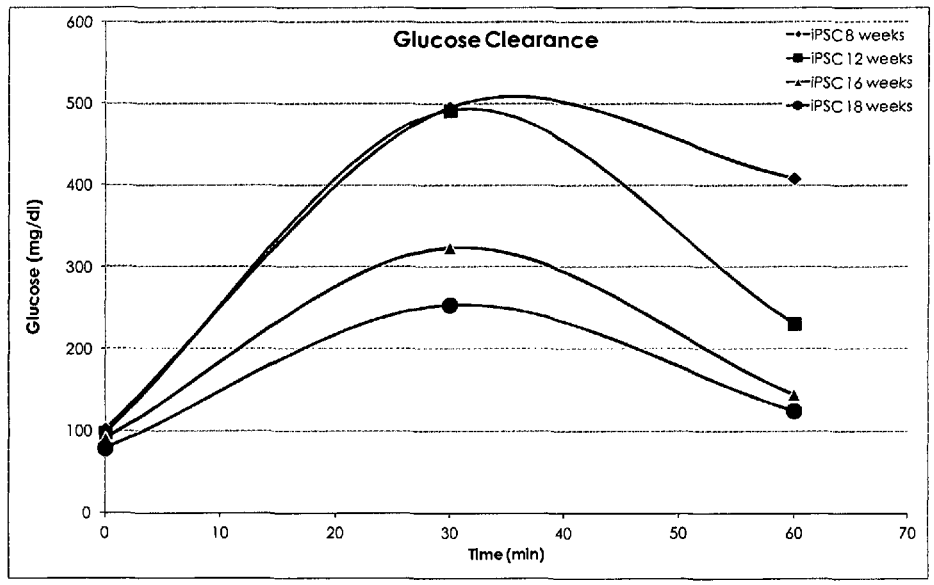
FIG. 12 shows glucose clearance (i.e. glucose levels at times in minutes following glucose stimulation) in mice at various times (in weeks) after implantation with a device as described herein comprising human pancreatic progenitor cells which had been pre-differentiated from human iPSCs.

The progenitors were loaded into devices manufactured with several different membrane types in order to evaluate the best setup for optimal cell survival, vascularization, and functional islet-cell differentiation. The cell-loaded devices were implanted subcutaneously in immunocompromised mice. Animals receiving the encapsulated grafts responded to glucose stimulation and produce human C-peptide (FIG. 11) and show faster glucose correction (FIG. 12).

In summary, these results demonstrate that pancreatic progenitors can be differentiated in vitro from human iPSCs, and encapsulated into a device as described herein. The encapsulated cells were further differentiated and matured in vivo into glucose responsive functional islet cells. These results enable development of IPSC-derived humanized pancreatic models for further investigation of genome versus function relationships.

All publications mentioned in the above specification are herein incorporated by reference. Various modifications and variations of the described embodiments of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in cell biology, biomedical engineering, and biotechnology or related fields are intended to be within the scope of the following claims.

Example 3

Figure 13:
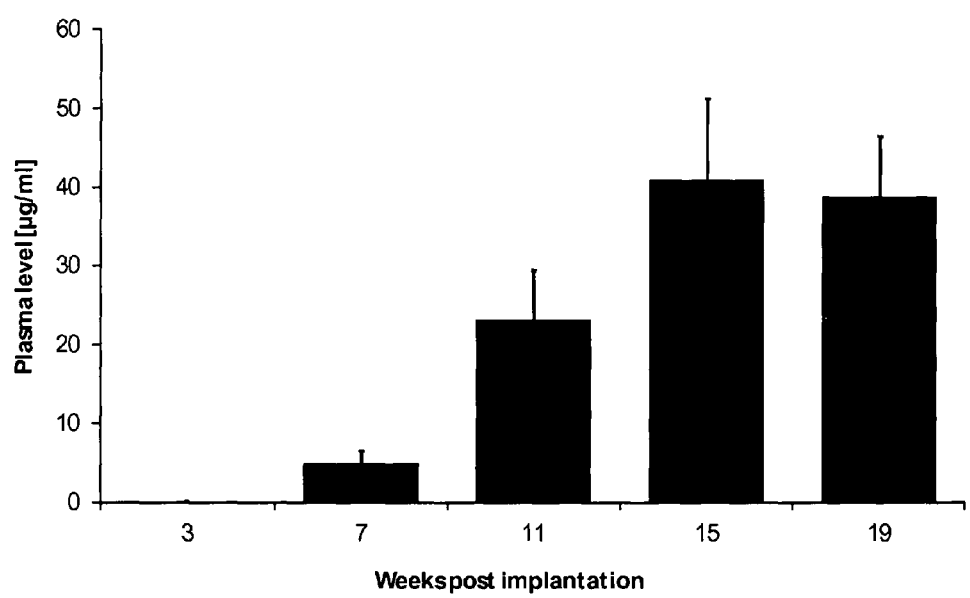
FIG. 13 shows antibody plasma level achieved by encapsulated engineered cells after subcutaneous implantation in mice.

Implantation of genetically engineered cell lines can be used to chronically deliver therapeutic proteins in vivo. The C2C12 mouse myoblast cell line was genetically engineered to secrete a therapeutic antibody. Cells were loaded into devices at a low density. The cell-loaded devices were implanted subcutaneously in adult mice under allogeneic conditions. Antibody plasma level was quantified from blood samples using a specific ELISA. Seven weeks after implantation, antibody was detected in mouse plasma. After 15 weeks, antibody level stabilized at approximately 40 µg/ml (see FIG. 13). Implants were retrieved after 19 weeks in vivo, and secretion level in vitro was measured. Devices were secreting in average 119 µg/24 hrs (±66 µg/24 hrs). Histological analysis revealed C2C12 cells surviving inside the device chamber at very high density.

In summary, these results demonstrate that a device of the present invention can sustain the progressive expansion and the survival of large amount of engineered cells over the long-term. As a consequence, therapeutic antibody plasma level can be achieved. These results validate the use of immunoisolated allogeneic genetically engineered cell line as an alternative method for the delivery of therapeutic recombinant protein.

The invention claimed is:

1. A biomolecular encapsulation device comprising an internal chamber suitable for holding living cells, wherein the internal chamber is disposed between an inner surface of a first semi-permeable layer and an inner surface of a second semi-permeable layer, and the first and second semi-permeable layers are mounted on a supporting frame surrounding a perimeter of the internal chamber; wherein the supporting frame comprises a first frame element that is interconnected to a second frame element, and the first and second frame elements co-operate to position the first and second semi-permeable layers at a predetermined separation distance between the layers
   wherein the first frame element comprises (a) a first mounting region to which an outer surface of the first semi-permeable layer is attached and (b) a first spacer region that is unitary with the first mounting region, and
   wherein the second frame element comprises (a) a second mounting region to which an outer surface of the second semi-permeable layer is attached and (b) a second spacer region that is unitary with the second mounting region,
   such that when the first and second frame elements interconnect the first and second spacer regions are positioned between the first and second mounting regions and together define the predetermined separation distance between the layers.

2. A device according to claim 1, wherein the first semi-permeable layer is mounted on the first frame element and the second semi-permeable layer is mounted on the second frame element, and the first and second frame elements interconnect to enclose the perimeter of the internal chamber.

3. A device according to claim 1, wherein the first and second frame elements are ultrasonically welded together.

4. A device according to claim 1, wherein the first and/or second semi-permeable layer is ultrasonically welded to the frame.

5. A device according to claim 1, further comprising an adhesive seal between the first and/or second semi-permeable layer and the supporting frame.

6. A device according to claim 1, wherein the first and second frame elements of the supporting frame cooperate to form a loading port, through which substances can be introduced into the internal chamber.

7. A device according to claim 1, further comprising an anchoring means for positioning the device within a tissue in vivo.

8. A device according to claim 1, wherein the first and second semi-permeable layers each comprise a membrane layer in contact with the internal chamber and a mesh layer overlying the membrane layer to the exterior of the internal chamber.

9. A device according claim 8, wherein the membrane layer comprises polypropylene, polycarbonate, polyethylene terephthalate or polytetrafluoroethylene and/or the mesh layer comprises nylon, titanium, stainless steel, polyethylene terephthalate, polytetrafluoroethylene or polyester.

10. A device according to claim 1, suitable for holding mammalian cells encapsulated in the internal chamber.

11. A device according to claim 10, wherein the encapsulated cells are human cells.

12. A device according to claim 10, wherein the encapsulated cells are cells which are capable of further maturation or differentiation in said device when implanted in vivo in a living mammal.

13. A device according to claim 10, wherein the encapsulated cells are engineered to express a recombinant product.

14. A device according to claim 10, wherein the encapsulated cells are capable of producing a therapeutic agent.

15. A device according to claim 10, wherein the encapsulated cells are used for an immune tolerization or immunizing the recipient.

16. A device according to claim 1, wherein the first and second frame elements are substantially the same shape.

17. A device according to claim 1, wherein first and second mounting regions are configured such that the inner surface of the first or second semi-permeable layer is free of the respective mounting surface of the respective mounting region.

18. A method for differentiating cells, comprising encapsulating differentiable cells in a device as defined in claim 1, and implanting the device into a living mammal.

19. A method for expressing a recombinant product into a living mammal, comprising encapsulating of cells engineered to express a recombinant product in a device as defined in claim 1.

20. A method for producing a therapeutic agent into a living mammal, comprising encapsulating of cells engineered to produce a therapeutic agent in a device as defined in claim 1.

21. A method for inducing an immune tolerization or for immunizing a living mammal, comprising encapsulating immune tolerizing and/or immunizing cells in a device as defined in claim 1, and implanting the device into a living mammal.

22. A method according to claim 21, wherein the mammal is non-human.

23. A method according to claim 21, wherein the encapsulated cells are human cells.

24. A method according to claim 21, wherein the device is implanted subcutaneously, intrathecally, intraosseous or intracerebrally.

25. A method for differentiating cells, comprising encapsulating differentiable cells in a device as defined in claim 3, and implanting the device into a living mammal.

26. A method for differentiating cells, comprising encapsulating differentiable cells in a device as defined in claim 4, and implanting the device into a living mammal.

27. A method for differentiating cells, comprising encapsulating differentiable cells in a device as defined in claim 5, and implanting the device into a living mammal.

28. A method for differentiating cells, comprising encapsulating differentiable cells in a device as defined in claim 6, by introducing the cells into the internal chamber through the loading port, and implanting the device into a living mammal.

29. A method for differentiating cells, comprising encapsulating differentiable cells in a device as defined in claim 7, and implanting the device into a living mammal.

30. A method for differentiating cells, comprising encapsulating differentiable cells in a device as defined in claim 8, and implanting the device into a living mammal.

31. A method for differentiating cells, comprising encapsulating differentiable cells in a device as defined in claim 9, and implanting the device into a living mammal.

32. A method for differentiating cells, comprising encapsulating differentiable cells in a device as defined in claim 16, and implanting the device into a living mammal.

33. A method for differentiating cells, comprising encapsulating differentiable cells in a device as defined in claim 17, and implanting the device into a living mammal.

\* \* \* \* \*